US004001664B2

United States Statutory Invention Registration [19]

[11] Reg. Number: H1664

[45] Published: Jul. 1, 1997

Sudo et al.

[54] ANALYTICAL ELEMENT FOR IMMUNOASSAY AND METHOD FOR ITS PREPARATION

[75] Inventors: Yukio Sudo; Nobuhito Masuda, both of Saitama, Japan

[73] Assignee: Fuji Photo Film Co., Ltd., Kanagawa, Japan

[21] Appl. No.: 320,771

[22] Filed: Mar. 8, 1989

[30] Foreign Application Priority Data

| | | | |
|---|---|---|---|
| Mar. 9, 1988 | [JP] | Japan | 63-055589 |
| Mar. 10, 1988 | [JP] | Japan | 63-57308 |
| Mar. 17, 1988 | [JP] | Japan | 63-64121 |

[51] Int. Cl.[6] ..... G01N 33/543

[52] U.S. Cl. ..... 436/518; 436/524; 436/538; 435/287.2; 435/7.92

[58] Field of Search ..... 436/518, 524, 436/169, 170, 538, 805; 435/288, 7.9, 7.93; 422/55, 56

[56] References Cited

U.S. PATENT DOCUMENTS

| | | | |
|---|---|---|---|
| 4,066,403 | 1/1978 | Bruschi | 436/170 |
| 4,430,436 | 2/1984 | Koyama et al. | 436/531 |
| 4,446,232 | 5/1984 | Liotta | 435/7.93 |
| 4,447,529 | 5/1984 | Greenquist et al. | 436/530 |
| 4,855,108 | 8/1989 | Masuda et al. | 436/170 |
| 4,861,552 | 8/1989 | Masuda et al. | 436/524 |
| 4,870,005 | 9/1989 | Akiyoshi et al. | 435/7.93 |
| 4,975,366 | 12/1990 | Sudo et al. | 436/170 |

*Primary Examiner*—Gary L. Geist
*Assistant Examiner*—Joseph D. Anthony
*Attorney, Agent, or Firm*—McAuley Fisher Nissen Goldberg & Kiel

[57] ABSTRACT

A dry-type analytical element for immunoassay utilizing antigen-antibody reaction in which the antigenic component is isolated from the antibody component by incorporating both components in separate layers or separately in a layer using different solvents. The analytical element is excellent in sensitivity and accuracy, and the analytical operation is simple.

20 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ANALYTICAL ELEMENT FOR IMMUNOASSAY AND METHOD FOR ITS PREPARATION

BACKGROUND OF THE INVENTION

1. Field of the Invention

This invention relates to an analytical element for immunoassay utilizing antigen-antibody reaction and preparation thereof.

2. Description of the Prior Art

Recently, analytical methods using dry-type analytical elements have been developed. In a dry-type analytical element, generally, an analyte, such as a biochemical substance contained in a body fluid, is allowed to react with reagent(s) incorporated in the analytical element. The amount of a particular reaction product or unreacted component is then determined by measuring the coloring, discoloring, fluorescence, luminescence or the like, optically, such as by spectrophotometry, to determine the content of the analyte. By using the dry-type analytical element, a particular component, such as a biochemically active substance, in a liquid sample can be analyzed simply, rapidly and acurately.

On the other hand, an immunoassay utilizing a dry-type analytical element has been reported in U.S. Pat. Nos. 3,992,158 and 4,459,358, German Patent Application 3 343 695A.

The antigen-antibody reaction in the field of immunology is the reaction in which an antibody or antigen specifically reacts with the corresponding antigen or antibody alone. It is widely utilized for the diagnosis of diseases of autoimmune system, detection of a trace component in a living body and the like. However, since methods utilizing antigen-antibody reactions require significant operational skills, it has been desired in the field of clinical tests to develop a measuring method requiring only simple operations which produces accurate results.

The method of measuring an antigen disclosed in EP 979 52A is a typical method utilizing a multilayer analytical element. This analytical element is composed of a spreading layer containing an antigen labeled with a fluorescent material, a partition layer composed of a porous medium and a reaction layer containing an immobilized antibody. The amount of the antigen is determined in this element by measuring the decrease of fluorescence intensity, utilizing the competitive antigen-antibody reactions between the antigen in a sample solution and the labeled antigen.

As another immunoassay method having a relatively high sensitivity, enzyme immunoassay (EIA) is known. A typical EIA is the solid phase competitive reaction method comprising allowing the antigen to be measured and an enzyme-labeled antigen or its analogue to react competitively with immobilized antibody, conducting bound-free (B/F) separation, and measuring the activity of either the enzyme bound to the antibody or the free enzyme to determine the amount of the antigen to be measured. In order to eliminate the B/F separation, an enzyme whose activity increases or decreases by binding to the antibody is necessary.

In order for these measuring systems to work effectively, two components, i.e. an enzyme-labeled antigen or its derivative and an immobilized antibody in one case, or an enzyme labeled antibody or its derivative and an immobilzed antigen in the other case, are necessary. In either case, these two components should be isolated so as not to react with each other before measuring. Satisfactory analytical sensitivity was not obtained in most of the known dry-type analytical elements because of a low signal/background ratio caused by insufficient isolation of the two components.

SUMMARY OF THE INVENTION

An object of the invention is to provide an immunological analytical element having a high analytical sensitivity and accuracy, and a method of preparation thereof.

Such an object has been achieved by isolating the antigen from the antibody in the layers composing the element or in the incorporating process.

Thus, the present invention provides a method for preparing a dry-type analytical element for immunoassay using an antigen-antibody reaction, said element comprising at least one water-permeable porous layer and containing an antigen homologue and a labeled antibody as the components participating in the antigen-antibody reaction in said porous layer, which comprises applying to the layer a composition containing said antigen homologue and a composition containing said labeled antibody separately or impregnating the porous layer with these compositions separately.

The present invention also provides a method for preparing a dry-type analytical element for immunoassay using an antigen-antibody reaction and comprising at least two integrated water-permeable layers, the water-permeable layers containing components participating in the antigen-antibody reaction, one of said components being an antigen conjugate, the other of said components being a labeled antibody, wherein at least one of the water-permeable layers is a porous layer, said porous layer containing one of said components but substantially not containing the other component, and a water-permeable layer located farther than the porous layer from the liquid-receiving face of the analytical element contains the other of the components but substantially does not contain the component contained in said porous layer.

The present invention further provides a method of preparing a dry-type analytical element for immunoassay using an antigen-antibody reaction and comprising at least two integrated water-permeable layers, the water-permeable layers containing components participating in the antigen-antibody reaction, one of said components being a labeled antigen, another of said components being an antibody, to said labeled antigen and to an unlabeled antigen, wherein at least one of the water-permeable layers is a porous layer, said porous layer containing the labeled antigen but substantially not containing the antibody, and a water-permeable layer located farther than the porous layer from the liquid-receiving face of the analytical element contains the antibody but substantially does not contain the labeled antigen.

DETAILED DESCRIPTION OF THE INVENTION

Figure 1:
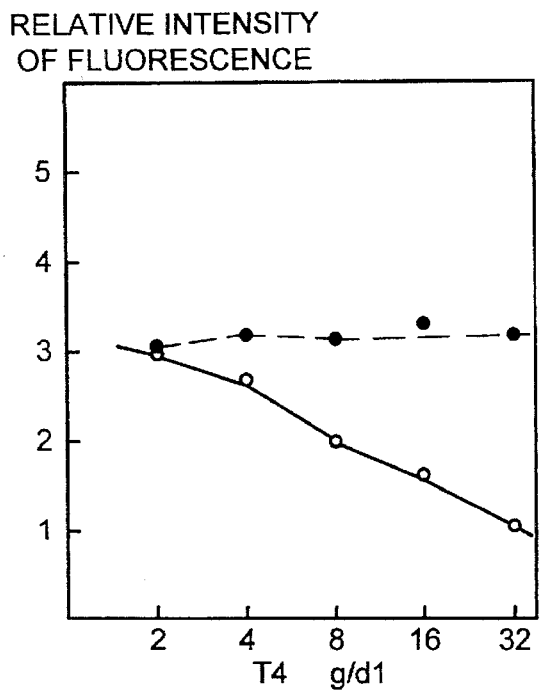
FIGS. 1 through 4 indicate a relation between the concentration of thyroxine or theophylline and fluorescence intensity or absorbance obtained by using the analytical element of the invention.

The analytical element of the invention contains the components participating in the antigen-antibody reaction including a combination of an antigen homologue and a labeled antibody or a combination of a labeled antigen and an antibody. The antibody, irrespective of labeled or unlabeled, should react to bind to the antigen homologue or the labeled antigen and an unlabeled antigen. The unlabeled antigen is usually the antigen to be measured contained in a sample, and the antigen conjugated or labeled is, in common, the antigen similar to the unlabeled antigen. The reactive site of the antibody to the above two antigens may be common to or different from each other. That is, when at least one of the above antigens has two or more antigenic determinants, the antibody may react at different sites. The antibody may be a monoclonal antibody. It may also be a pepsin-digestion product of the antibody, such as $F(ab')_2$ or Fab'. The antigen homologue is a substance capable of binding to an antibody like an antigen, and includes conjugate of an antigen or its fragment with a protein, latex or solid carrier.

The components participating in the antigen-antibody reaction involving the antigen homologue can be explained as follows:

1) In the case of utilizing the function of analyte as an antigen:

The analyte is an antigen, and in this case, the labeled antibody means a conjugate of an antibody or its fragment having a binding force specific to the antigen and a detectable substance. The antigen homologue means a substance having a binding force similar to the above antigen. As a result, the analyte and the antigen homologue competitively bind to the labeled antibody. For example, when the analyte is theophylline, an example of the labeled antibody is alkaline phosphatase-labeled anti-theophylline antibody, and an example of the antigen homologue is theophylline BSA. When the analyte is human IgE, an example of the labeled antibody is glucose oxidase-labeled anti-human IgE antibody, and an example of the antigen homologue is a human IgE immobilized with latex.

2) In the case that the analyte is a specific antibody and its function as the antibody are utilized:

The analyte is an antibody, and in this case, the antigen homologue means a fragment of a partner or its derivative of the antibody specifically bonded thereto. The labeled antibody means a conjugate of an antibody or its fragment having a binding force to the antigen homologue like the antibody which is the analyte. As a result, the analyte and the labeled antibody competitively bind to the antigen homologue. For example, when the analyte is anti-HBs antibody, an example of the labeled antibody is FITC-labeled anti-HBs antibody and an example of the antigen homologue is HBs antigen-immobilized polystyrene beads.

The label substance may be fluorescent materials, luminescent materials, enzymes, and other known labels used for immunoassay.

The fluorescent materials include the fluorescent materials having amino group, such as, 1-aminostilbene, 2-aminonaphthalene, p,p'-diaminostilbene, 2-aminoacridine, p,p'-diaminobenzophenone imines, bis-3-aminopyridinium salts and indoles and fluorescent phenols, such as, 7-hydroxycoumalins, 3,6-dihydroxyxanthenes, tetracycline and salicylic acid esters. A representative fluorescent material is fluorescein.

The luminescent materials includes chemiluminescent materials, such as, 2,3-dihydro-1,4-phthlazinediones represented by luminol and 2,4,5-triphenylimidazoles.

Various enzymes can be employed as the label. Suitable enzymes are selected by considering the activity, stability, influence of binding upon the activity, the availability of a simple measuring method of enzyme acitivity. Examples of the enzymes are described in Table 1 and Table 2 of U.S. Pat. No. 4,501,692, and representative enzymes are glucose oxidase (GOD), β-D-galactosidase, peroxidase (POD), alkaline phosphatase (ALP), α-amylase, luciferase, etc.

The binding method of the label substance to the antigen or the antibody may be conventional as described, for example, in "Koso-Meneki Sokutei-Ho (Enzyme Immunoassay) (2nd. Ed.)" (Ishikawa et al., 1982), "Rinsho Kensa Gijutsu Zensho 4, Meneki Kessei Kensa (Clinical Assay Technique Complete Book 4 Immune Serum Assay)", pages 97–102 (Ed. Kawai, Igaku-Shorin, 1977), Biochem. Biophys. Res. Commun., 74, 538 (1977), Clinica Chimica Acta, 83, 161 (1973), etc.

The examples of the labeled antigens are also described in the above references. Specific examples are fluorescein isocyanate-bound thyroxine (FITC-T4), GOD-bound human immunoglobulin (IgG), ALP-bound IgG, POD-labeled α-fetoprotein and the like.

The examples of the labeled antibodies are fluorescein isocyanate-bound thyroxine (FITC-T4) antibody, GOD-bound anti-human immunoglobulin (IgG) antibody, ALP-bound anti-IgG antibody, POD-labeled anti-α-fetoprotein antibody and the like.

In the case of using an enzyme-labeled antibody or an enzyme-labeled antigen, the measurement of the enzyme activity is necessary in order to measure the result of the antigen-antibody reaction, and therefore, a substrate of the enzyme and a detection system of the enzyme reaction product are necessary. The substrate is preferably incorporated into a different layer from the layer containing the labeled antibody or the labeled antigen. At least, either the substrate or the enzyme-labeled antibody or antigen is preferably applied to the layer by using a solvent substantially not initiating the enzyme reaction of the enzyme-labeled antibody or antigen. The substrate and the detection system of the enzyme reaction product may be incorporated into the same layer or different layers from each other. In the case that the substrate is a self color-developing type substrate, the system for detecting the enzyme reaction product is not necessary.

The analytical elements of the invention are classified into a type of the analytical element comprising at least one water-permeable porous layer and two types of the analytical element comprising at least two integrated water-permeable layers.

In the former case, a composition containing the antigen homologue is separately applied to the same porous layer from a composition containing the labeled antibody, by coating or impregnating.

The solvent in the composition first applied dissolves or suspends the component participating in the antigen-antibody reaction, i.e. the antigen homologue or the labeled antibody incorporated in the above first composition. Preferable solvents are those which dissolve the above component, and water is usually the most preferable. Suitable concentration of the component varies depending on the kind of the component, the solvent and the like.

The first composition may contain reagents for fluoroimmunoassay, EIA or the like other than the antigen homologue or the labeled antibody described above. Such reagents are preferably soluble in the above described solvents and include color-forming reagents, buffers, etc.

The buffers suitable for the analytical element of the invention are carbonate buffers, borate buffers, phosphate buffers, Good's buffers, and the like. Such a buffer may be selected with reference to "Tanpakushitsu Koso no Kiso-Jikken-Ho (Fundamental Experimental Method of Proteins, Enzymes)" (Horio et al., Nanko-Do, 1981), Biochemistry, vol. 5, No. 2 pp 467–477, 1966, or the like.

The first composition may also contain the usual additives for known analytical elements, such as a surfactant and light-reflective particles.

The composition applied to or impregnating the layer later contains the other member of the components participating in the antigen-antibody reaction and a solvent therefor. That is, if the first composition contains an antigen conjugate, the second composition contains a labeled antibody. Conversely, if the first composition contains a labeled antibody, the second composition contains an antigen conjugate.

The solvent in the above second composition dissolves or suspends the component participating in the antigen-antibody reaction incorporated in the second composition, and it does not substantially dissolve the component incorporated in the first composition. Preferably, it does not swell the hydrophilic polymeric substances, such as protein, and its polarity is different from the solvent in the first composition. Examples of such a solvent are alcohols such as ethanol and methanol, ketones such as acetone and ethers such as ethyl cellosolve. Suitable concentration of the composition is varying according to the kind of the solvent and the like.

The second composition may contain other reagents for fluoroimmunoassay, EIA (enzymatic immunoassay) or the like, and the usual additives to known analytical elements, in addition to the component participating in the antigen-antibody-reaction incorporated in the first composition. They are preferably soluble in the solvent employed.

On the other hand, the above other reagents and additives may be incorporated into the porous layer in a step separate from the incorporation of the first and second compositions. In this case, they may be incorporated prior to applying or impregnating of the first composition. When the other reagents and additives are incorporated after applying to the layer, or immersing the layer in, the first composition, the solvent for the reagents and additives preferably has the above properties as the solvent for the second composition.

In the latter case of the analytical element comprising at least two integrated water-permeable layers, an embodiment includes a combination of an antigen homologue and a labeled antibody as the components participating in the antigen-antibody reaction. Another embodiment includes a combination of a labeled antigen and an antibody as the components participating in the antigen-antibody reaction. In these embodiments, one of the components is incorporated into the porous layer of the two integrated water-permeable layers, and the other is incorporated into the water-permeable layer located farther than the porous layer from the liquid-receiving face of the analytical element. As a method for incorporating the components into the layers, the water-permeable layer containing one of the components is provided, and the porous layer to which the composition containing the other of the components has been previously applied is integrally laminated to the water-permeable layer above. The lamination may be carried out, for example, by the method disclosed in EP 0 166 365A. In the above case, both of the solvent for the composition containing one of the components and the solvent for the composition containing the other of the components are selected without particular requirement. While, the composition containing the other of the components may be applied, by coating or immersion, to the porous layer after the lamination. The composition must neither dissolve nor solubilize any of the components contained in the water-permeable layer. A useful method is composed of providing a reagent layer containing one of the components and a hydrophilic polymer as binder by applying or the like, laminating integrally the porous layer thereon, and thereafter applying to the porous layer, by coating or immersion, the composition containing the other of the components but not swelling the hydrophilic polymer of the reagent layer. The composition not swelling the hydrophilic polymer includes organic solvent solutions, and examples of such a solvent are alcohols such as ethanol and methanol, ketones such as acetone and ethers such as ethyl cellosolve. Suitable concentrations of the composition are varying according to the kind of the solvent and the like.

Where both of the antigen homologue and the labeled antibody are incorporated into the same porous layer, the analytical element prepared by the method of the invention has at least one water-permeable porous layer. The porous layer may be disposed as the topmost layer or disposed between the topmost layer and the reagent layer. The porous layer may be a spreading layer having a metering action or other layers. The metering action is such that a sample spotted on the spreading layer spreads at a fixed amount per unit area with even distribution of any component in the sample in lateral directions. The porous layer may be composed of a fibrous material or a nonfibrous material, and includes woven fabrics, such as plain weaves and knitted fabrics, such as, tricot fabric made of natural, synthetic or semisynthetic fiber, nonwoven fabrics, filter papers, glass fiber filter paper, membrane filters composed of cellulose acetate or the like, bodies formed from agglomerated inorganic or organic particles, etc. Suitable porous layers include the fibrous layers described in U.S. Pat. No. 4,292,272 and EP 0 162 302A and the porous layers described in U.S. Pat. No. 3,992,158, EP 0 166 365A, Japanese Patent KOKAI 58-70163 and Japanese Unexamined Patent Publication (kokai) 62-116258, 62-138756, 62-138757 and 62-138758, woven fabrics and knitted fabrics being particularly preferable. The woven fabrics, etc., may be treated with glow discharge, such as disclosed in GB 2 087 074A. Besides, the spreading layer may contain a hydrophilic polymer or a surfactant described in EP 0 162 302A and Japanese Unexamined Patent Publication (kokai) 63-112999, 63-219397 and 62-182652 in order to adjust spreading area, spreading speed and the like. In the above method, the first composition is first applied to the porous layer by coating or immersion, and thereafter the second composition is applied to the same porous layer by coating or immersion. The application or the impregnation of both compositions may be carried out by a known method, such as dip coating, doctor coating, hopper coating, extrusion coating or curtain coating. The analytical element prepared by the above method may comprise at least two water-permeable layers, at least one being a porous spreading layer. The other layer of the above water-permeable layers is located on the opposite side to the sample-receiving surface of the above porous spreading layer, and the porous spreading layer contains the antigen homologue and the labeled antibody as the components participating in the antigen-antibody reaction. In this case, the first composition and the second composition may be separately applied to the porous spreading layer by coating or immersion, and this spreading layer may thereafter be bound to the other water-permeable layer by the method described in U.S. Pat. No. 4,292,272 or the like. Also, the porous spreading layer coated or impregnated with the first composition may be bound to the other water-permeable layer by the above method or the like, and thereafter, the second composition may be applied to the spreading layer. In addition, the analytical element prepared by the method of the invention may comprise at least two water-permeable porous layers. One of the two porous layers is a spreading layer, and the other is a reagent layer located on the side of the spreading layer opposite to the sample-receiving side. The reagent layer contains the antigen homologue and the labeled antibody as the components participating in the antigen-antibody reaction. In this case, the first composition and the second composition are first separately applied to the spreading layer by coating or immersion, and this spreading layer may be bound to the reagent layer by the method described above or the like. Where an enzyme is the label substance, a substrate for the enzyme, an oxidizing agent, a coupler, a buffer, etc. may be incorporated into the reagent layer. Among those, the substrate must to be incorporated.

On the other hand, when the two essential components participating in the antigen-antibody reaction are incorporated into separate layers, the analytical element of the invention comprises at least two integrated water-permeable layers containing at least one porous spreading layer. The other layer of the above two water-permeable layers is located on the opposite side to the sample-receiving side of the above porous spreading layer.

Alternatively, the above analytical element may comprise at least two water-permeable porous layers. One of the above two porous layers is a spreading layer, and the other is a reagent layer located on the side of the above spreading layer opposite to the sample-receiving side. Where an enzyme is the label substance, a substrate for the enzyme must be, and an oxidizing agent, a coupler, a buffer, etc. may be incorporated into the reagent layer.

In the analytical element of the invention, the spreading layer may also function as a reagent layer, or a reagent layer may be independently provided. The reagent layer may be a uniform layer containing a hydrophilic polymer as a binder such as gelatin, its derivatives such as phthalated gelatin, cellulose derivatives such as hydroxymethyl cellulose, agarose, polyacrylamide, polymethacrylamide and copolymers of acrylamide or methacrylamide and various vinyl monomers. The reagent layer may also be composed of a porous material such as disclosed in EP 0 166 365A, Japanese Patent KOKAI 58-70163 and Japanese Unexamined Patent Publication Nos. 62-116258, 62-138756, 62-138757 and 62-138758.

One or more other layers may be incorporated into the analytical element of the invention. Examples of such layers include a binding layer, a light-blocking layer and a filtering layer. Moreover, each of the porous reagent layers mentioned previously may be composed of two or more layers, respectively. Examples of the analytical element to which the present invention is applicable are disclosed in U.S. Pat. No. 3,992,158, U.S. Pat. No. 4,042,335, U.S. Pat. No. 4,292,272, EP 0 226 465A, and Japanese Patent KOKAI 62-138757 and 62-138758.

The registration layer is a layer in which the dye produced in the presence of an analyte can diffuse and is optically detected through a light-transmissive support. This layer may be composed of a hydrophilic polymer, and may contain a mordant for the dye, such as a cationic polymer for an anionic dye.

The water absorption layer is a layer in which the dye produced in the presence of an analyte substantially does not diffuse, and may be composed of a hydrophilic polymer readily swellable.

The binding layer is provided in order to adhere the porous layer to another layer, and it is preferably composed of a hydrophilic polymer capable of adhering the porous layer when the polymer is in wet, swollen state. Such a hydrophilic polymer includes gelatin, gelatin derivatives, polyacrylamide and starch. The binding layer may also be provided on the aforementioned reagent layer, another reagent layer, light-blocking layer, filtering layer, water absorption layer, registration layer or the like.

The light-blocking layer blocks the color of the sample stotted on a spreading layer, particularly the red color of hemoglobin in a whole blood sample, when the optically detectable change such as coloration or discoloration, occurring in the reagent layer, a registration layer or the like, is measured by reflection photometry from the side opposite to the spreading layer. In addition, it also functions as a light-reflection or background layer. The light-blocking layer is preferably a light-reflecting layer being water-permeable composed of a hydrophilic polymer as a binder wherein light-reflecting particles, such as titanium dioxide or barium sulfate, are dispersed. Preferable hydrophilic polymers are gelatin, gelatin derivatives, polyacrylamide and the like. The light-reflecting particles may also be incorporated into the spreading layer, the reagent layer, a resistration layer or the like in addition to or instead of the light-blocking layer.

The following embodiments are practically employable as the analytical element of the invention provided it contains a light-transmissive water impermeable support:

(1) The spreading layer, the reagent layer and the support, superposed in this order.

(2) The spreading layer, the reagent layer, a registration layer and the support, superposed in this order.

(3) The spreading layer, a light-reflecting layer, the reagent layer and the support, superposed in this order.

(4) The spreading layer, a light-reflecting layer, the reagent layer, a registration layer and the support, superposed in this order.

(5) The spreading layer, the reagent layer, a light-reflecting layer, a registration layer and the support, superposed in this order.

(6) The spreading layer, a first reagent layer, a light-reflecting layer, a second reagent layer and the support, superposed in this order. One or both of the above reagent layers contain the labeled antigen.

(7) The spreading layer, a first reagent layer, a light-reflecting layer, a second reagent layer, a registration layer and the support, superposed in this order. One or both of the above reagent layers contain the labeled antigen.

In the above embodiments of (1) to (5), the reagent layer may be composed of different two or more layers. A water absorption layer may be provided between the reagent layer or the registration layer and the support. In the embodiments of (1) to (3) and (6), a filtering layer may be provided between the reagent layer and the registration layer or the spreading layer. In the above embodiments of (3) to (7), a filtering layer may also be provided between the light-reflecting layer and the registration layer, the spreading layer and the reagent layer, the reagent layer and the registration layer, or the spreading layer and the reagent layer. In the case that the reagent layer is composed of two or more layers, a filtering layer may also be provided between them.

A preferable material for the support is polyethylene terephthalate. In order to increase the adhesive strength, the support may be provided with undercoating layer, or the surface of the support may be treated so as to increase hydrophilic property.

The antigen homologue and the labeled antibody may be incorporated into the spreading layer or the reagent layer.

In the case of using an enzyme-labeled antibody or an enzyme-labeled antigen, the reagent composition for the determination of an enzyme reaction product may be incorporated into the layer containing the labeled antibody or antigen or into another nonporous or porous layer. For example, a composition producing an intermediate product by the reaction with an enzyme-reaction product is incorporated into a first reagent layer, and a composition, such as an indicator, producing a dye by the reaction with the intermediate product is incorporated into a second reagent layer interposed between the first reagent layer and the support. The composition producing the intermediate product may be incorporated into a layer, such as a spreading layer or a light-reflecting layer, farther than a reagent layer from the support, and the indicator is incorporated into the reagent layer.

EXAMPLES

Example 1

(1) Synthesis of T4-BSA 15 mg of bovine serum albumin (BSA) was dissolved in 3 ml of 0.1M phosphate buffer solution of pH 8.0, and a T4 solution containing 10 mg of thyroxine (T4) dissolved in 3 ml of dimethyl sulfoxide was gently added to the BSA-buffer solution. 0.2 ml of 1% glutaraldehyde solution was slowly added to the mixed solution, and allowed to react at 4° C. for 3 hours. The reaction solution was dialyzed for 2 days, and lyophilized to obtain a T4-BSA conjugate.

(2) Preparation of Antigen-Immobilized Membrane A nitrocellulose membrane filter (Millipore Co.) was immersed in the following Solution A overnight, and washed well with water.

| | | |
|---|---|---|
| Solution A: | T4-BSA | 15 μg |
| | Carbonate buffer solution (pH 9) | 10 ml |

Subsequently, the membrane filter was immersed in a solution containing 300 mg of BSA dissolved 10 ml of water, and allowed to stand overnight. Then, it was washed well with water, and dried at a room temperature to obtain the antigen-immobilized membrane.

(3) Preparation of Element for Measuring T4

The above antigen-immobilized membrane was immersed in the following Solution B, and rapidly dried.

| | |
|---|---|
| anti-T4 antibody solution containing 40 μg of dry powder of the antibody | 1 ml |
| Ethanol | 9 ml |

Subsequently, the membrane was laminated by joining at a number of dots to polyethylene terephthalate (PET) support of 180 μm in thickness according to the method disclosed in EP 0 226 465A, and cut into square pieces having a side of 15 mm. Each piece was put between polystyrene frames having a window of 10 mm in diameter to obtain the element I for measuring T4.

On the other hand, a comparative element II for measuring T4 was prepared in the same manner as the element I for measuring T4, except that the following Solution C was used instead of Solution B.

| | | |
|---|---|---|
| Solution C: | FITC-labeled anti-T4 antibody solution containing 40 μg of dry powder of the antibody | 1 ml |
| | Distilled Water | 9 ml |

(4) Measurement of Thyroxine

Various known amounts of T4 were added to a serum not containing T4 to obtain sera containing various known amounts of T4. 5 μl of 0.3M glycine buffer solution of pH 9.0 containing 0.05M sodium dodecylnaphthalenesulfonate was added to 5 μl of each T4-containing serum, and spotted onto each analytical element. After the analytical elements were allowed to stand at 37° C. for 15 minutes, free FITC-labeled antibody was washed off by repeating twice the operation in which 15 μl of the 0.3M glycine buffer solution same as above was dropped to each analytical element followed by wiping off.

Thereafter, the fluorescence at a wave length of 525 nm emitted from each analytical element was measured from the PET support side by using a fluorophotometer ("Fluorophotometer 650-10(s)", Hitachi Ltd.) at an excitation wave length of 495 nm.

The results are shown in FIG. 1. In the drawing, open circle indicates the element I for measuring T4, and closed circle indicates the comparative element II for measuring T4. As shown in the drawing, the analytical element I of the invention showed a good correlation between T4 concentration and fluorescence intensity, whereas, in the case of the comparative analytical element II, fluorescence intensity hardly varies, when T4 concentration was varied.

Example 2

(1) Preparation of Antigen-Immobilized Membrane

T4-BSA conjugate was prepared and immobilized to nitrocellulose membrane filter to obtain the antigen-immobilized membrane, in the same manner as Example 1.

(2) Preparation of FITC-Labeled Antibody-Containing Membrane (Cloth)

A tricot fabric composed of PET spun yarn was immersed in Solution C same as prepared in Example 1, and then dried to obtain the FITC-labeled anti-T4 antibody-containing membrane.

(3) Preparation of Element for Measuring T4

To a PET support of 180 μm in thickness, the antigen-immobilized membrane was laminated, and the labeled antibody-containing membrane was further laminated thereon, by joining at dots according to the method disclosed in EP 0 226 465A, respectively. The laminate was cut into square pieces having a side of 15 mm. Each piece was put between polystyrene frames having a window of 10 mm in diameter to obtain the element III for measuring T4.

(4) Measurement of Thyroxine

In the same manner as Example 1, sera containing various known amounts of T4 were prepared, and the measurement of T4 of each serum was carried out using the above element III.

Figure 2:
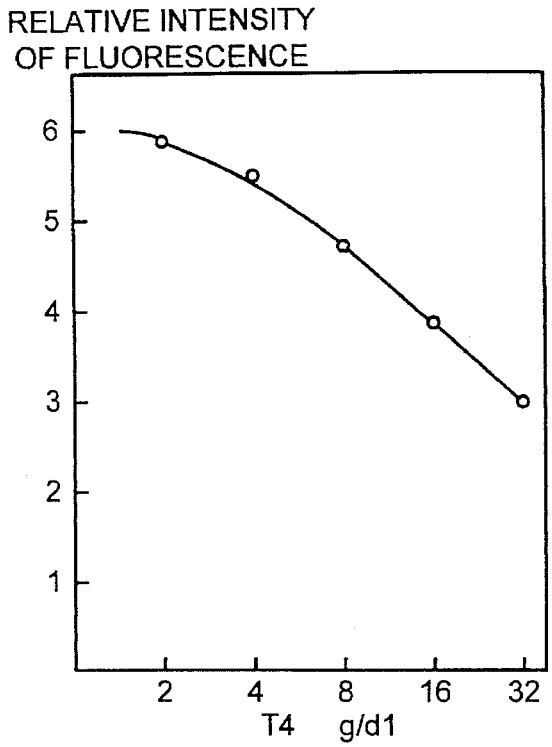

The results are shown in FIG. 2. As shown in the drawing, the analytical element III of the invention showed a good correlation between T4 concentration and fluorescence intensity.

Example 3

(1) Synthesis of Fluorescein-Labeled Thyroxine

Fluorescein isocyanate-labeled thyroxine (FITC-T4) was synthesized according to the method disclosed in Japanese Patent KOKAI No. 59-170768.

(2) Preparation of Antiserum-Containing Sheet

The following Solution E was coated on a gelatin-subbed colorless transparent smooth PET film of 180 μm in thickness so as to obtain a dry thickness of 2 μm on drying to form a water absorption layer.

| | | |
|---|---|---|
| Solution E: | Gelatin | 10 g |
| | Formalin | 0.2 g |
| | Water | 90 g |

The water absorption layer was moistened with 20 g/m$^2$ of water, and a cellulose acetate membrane filter ("Microfilter FM 300", Fiji Photo Film Co., Ltd.) was pressed on it to laminate it.

The following Solution F was coated on the membrane filter at a rate of 100 cc/m$^2$, and dried to obtain the antiserum-containing sheet I.

| | | |
|---|---|---|
| Solution F: | Anti-thyroxine antiserum | 5 μl |
| | Nonylphenoxypolyethoxyethanol | 0.04 mg |
| | Water | 100 ml |

(3) Preparation of FITC-T4-Containing Sheet

A tricot fabric made by knitting 50 deniers PET spun yarn at 36 gauge was immersed in the following Solution G, and dried to obtain the FITC-T4-containing sheet.

| | | |
|---|---|---|
| Solution G: | FITC-T4 | 24 μg |
| | Polyvinylpyrrolidone | 5 g |
| | Nonylphenoxypolyethoxyethanol | 0.1 mg |
| | Water | 200 ml |

(4) Preparation of Multilayer Sheet

The FITC-T4-containing sheet was laminated to the membrane filter layer of the antiserum-containing sheet I by joining at dots according to the method disclosed in EP 0 226 465A to obtain the multilayer sheet for measuring T4.

(5) Measurement of Thyroxine

A serum was treated with activated carbon to obtain a serum not containing T4, and various known amounts of T4 were added to the serum. 7.5 μl of 0.3M glycine-NaCl-NaOH buffer solution and 7.5 μl of blocker solution (aqueous 0.1M sodium dodecylnaphthalenesulfonate) were added to 15 μl of the serum containing T4 in various concentration, and each 30 μl of the mixed solution was dropped to the multilayer analytical element obtained in the above paragraph (4). After the analytical element was allowed to stand at 25° C. for 30 minutes, the fluorescence at a wave length of 525 nm emitted by each analytical element was measured through the PET support by using a fluorophotometer ("Fluorophotometer 650-10(s)", Hitachi Ltd.) with excitation at a wave length of 495 nm.

Figure 3:
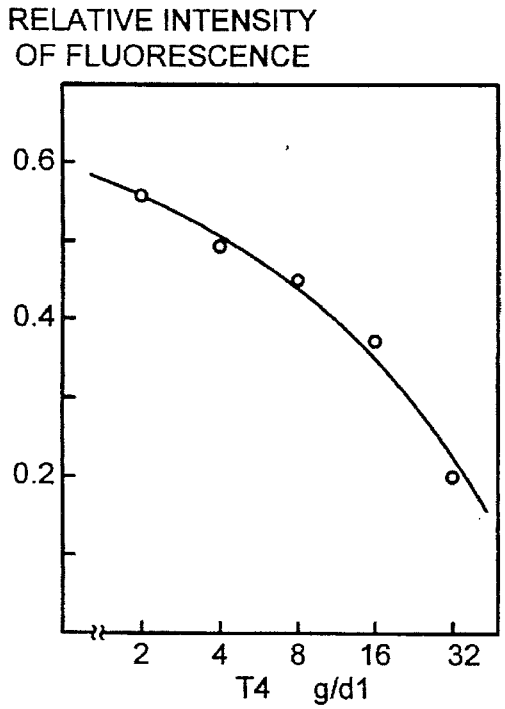

The results are shown in FIG. 3.

Example 4

(1) Coating of Antibody

The following Solution H was applied on a PET support having a thickness of 180 μm at a rate of 90 cc/m$^2$, and dried.

| | | |
|---|---|---|
| Solution H: | Gelatin | 25 g |
| | Surfactant ("Surfactant 10 G", Olin) | 2 g |
| | Nitrotetrazolium Blue (NTB) | 3.2 g |
| | Distilled Water | 444 g |

The following Solution I was applied thereon at a rate of 100 cc/m$^2$, and a polyester knitted fabric treated with glow discharge was laminated thereon after the setting of gelatin and allowed drying.

| | | |
|---|---|---|
| Solution I: | Gelatin | 20 g |
| | Nonylphenoxypolyethoxyethanol | 2 g |
| | Citric acid | 3 g |
| | 1% Diaphorase solution | 20 g |
| | Water | 260 g |
| | pH 7.7 | |

Subsequently, the whole amount of Reagent A of the theophylline 100 assay kit "EMIT" (Syva Co., U.S.A.) was dissolved in an aqueous solution containing 2 g of polyvinyl pyrrolidone dissolved in 12 ml of distilled water. The above theophylline antibody solution was applied on 800 cm$^2$ of the polyester knitted fabric, and dried to obtain the lower part of a multilayer immunological analytical element.

(2) Incorporation of Labeled Antigen

The whole amount of Reagent B of the theopylline 100 assay kit "EMIT" (Syva Co., U.S.A.) was dissolved in an aqueous solution containing 2 g of polyvinyl pyrrolidone dissolved in 20 ml of distilled water. A polyester knitted fabric treated with glow discharge was immersed in the above solution, and dried to obtain a labeled antigen-containing sheet.

(3) Preparation of Multilayer Immunological Element

The above labeled antigen-containing sheet was laminated onto the polyester knitted fabric of the lower part described above to complete the multilayer immunological analytical element.

(4) Meaurement of Theophylline

Figure 4:
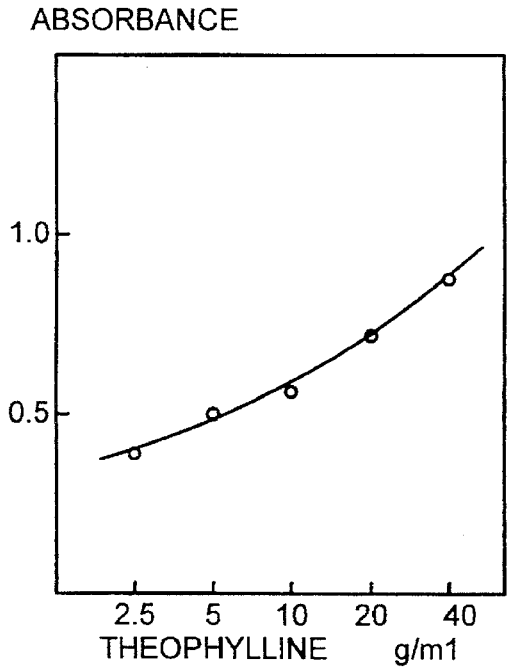

Respective analytical elements were cut into square pieces having a side of 15 mm, and each piece was interposed between the plastic frames each having a hole of 10 mm in diameter. Each calibrating solution containing 0, 2.5, 5, 10, 20 or 40 μg/ml of theophylline (serum calibrator, "EMIT" kit, Syva Co.) was mixed with the buffer solution incorporated in the same kit at the volume ratio of 1:4. Each 30 μl of the mixtures was spotted on respective analytical elements (5) and (6), reflection absorbance at a wave length of 540 nm was measured one minute and five minutes after the spotting by using an analyzer ("FUJI Drychem Analyzer FDC 1000", Fuji Photo Film Co., Ltd.). The results are shown in FIG. 4 as the difference between the reflection absorbance measured after one minute and that after five minutes. As shown in the drawing, a good calibration curve was obtained between 2.5 and 40 μg/ml of theophylline in a serum.

We claim:

1. A dry analytical element for immunoassay using an antigen-antibody reaction and comprising at least two integrated water-permeable layers, the water-permeable layers containing components participating in the antigen-antibody reaction, one of said components being an antigen, the other of said components being a labeled antibody, wherein at least one of the water-permeable layers is a porous layer, said porous layer containing one of the components but not containing the other component, and a water-permeable layer located distal from the liquid-receiving face of the analytical element as compared to the porous layer, and which contains the other of the components but does not contain the component contained in such porous layer.

2. The analytical element of claim 1 wherein the labeled antibody is contained in the porous layer and the antigen is contained in the distal water-permeable layer.

3. The analytical element of claim 1 wherein the antigen is contained in the porous layer and the labeled antibody is contained in the distal water-permeable layer.

4. The analytical element of claim 1 wherein the protein is albumin.

5. A dry analytical element for immunoassay using an antigen-antibody reaction and comprising at least integrated two water-permeable layers, the water-permeable layers containing components participating in the antigen-antibody reaction, one of said components being a labeled antigen, another of said components being an antibody to said labeled antigen and to an unlabeled antigen, wherein at least one of the water-permeable layers is a porous layer, said porous layer containing the labeled antigen but not containing the labeled antigen but not containing the antibody, and a water-permeable layer located distal from the liquid-receiving face of the analytical element as compared to the porous layer and which contains the antibody but not the labeled antigen.

6. The analytical element of claim 5 wherein said porous layer is a liquid-spreading layer of the element.

7. A method of preparing a dry analytical element for immunoassay using an antigen-antibody reaction and comprising at least two integrated water-permeable layers, the water-permeable layers containing an antigen and a labeled antibody at least one of the water-permeable layers being a porous layer, which comprises providing the porous layers on the water-permeable layer containing the antigen, and thereafter applying to the porous layer a composition containing said labeled antibody and not dissolving nor solubilizing said antigen.

8. A method for preparing a dry analytical element for immunoassay using an antigen-antibody reaction and comprising at least integrated two water-permeable layers, the water-permeable layers containing an antigen and a labeled antibody and at least one of the water-permeable layers being a porous layer, which comprises providing the porous layer to which a composition containing said labeled antibody is previously applied on the water-permeable layer which contains said antigen or its fragment.

9. A method for preparing a dry analytical element for immunoassay using an antigen-antibody reaction and comprising at least two integrated water-permeable layers, the water-permeable layers containing an antigen and a labeled antibody, and at least one of the water-permeable layers being a porous layer, which comprises providing the porous layer on the water-permeable layer containing the labeled antibody, and thereafter applying to the porous layer a composition which contains said antigen and not dissolving nor solubilizing said labeled antibody.

10. A method for preparing a dry analytical element for immunoassay using an antigen-antibody reaction and comprising at least two integrated water-permeable layers, the water-permeable layers containing an antigen and a labeled antibody, and at least one of the water-permeable layers being a porous layer, which comprises providing the porous layer, to which a composition which contains said antigen is previously applied, on the water-permeable layer containing said labeled antibody.

11. A method for preparing a dry analytical element for immunoassay using an antigen-antibody reaction and comprising at least integrated two water-permeable layers, the water-permeable layers containing a labeled antigen and an antibody to the labeled antigen and to an unlabeled antigen as the components participating in the antigen-antibody reaction, and at least on of the water-permeable layers being a porous layer, which comprises providing the porous layer on the water-permeable layer containing the antibody so that the water-permeable layer is located distal from the liquid-receiving face of the analytical element as compared to the porous layer, and thereafter applying to the porous layer a composition containing said labeled antigen and not dissolving nor solubilizing said antibody in the water-permeable layer.

12. A method for preparing a dry analytical element for immunoassay using an antigen-antibody reaction and comprising at least integrated two water-permeable layers, the water-permeable layers containing a labeled antigen and an antibody to the labeled antigen and to an unlabeled antigen as the components participating in the antigen-antibody reaction, and at least one of the water-permeable layers being a porous layer, which comprises providing the porous layer, to which a composition containing said labeled antigen is previously applied, on the water-permeable layer containing the antibody, so that the water-permeable layer is located distal from the liquid-receiving face of the analytical element as compared to the porous layer, and which contains the other of the components but does not contain the component contained in such porous layer.

13. A method for preparing a dry analytical element for immunoassay using an antigen-antibody reaction, said element comprising at least one water-permeable porous layer and containing an antigen and a labeled antibody as components participating in the antigen-antibody reaction in said porous layer, which comprises separately applying to the porous layer a composition containing said antigen and a composition containing said labeled antibody.

14. The method of claim 13, wherein the composition containing the antigen contains water as a solvent.

15. The method of claim 13, wherein the composition containing the labeled antibody contains a solvent from the group consisting of alcohols, ketones and ethers.

16. The method of claim 13, wherein the composition containing the labelled antibody contains a solvent from the group consisting of ethanol, methanol, acetone or ethyl cellosolve.

17. The method of claim 13 wherein, after the composition containing said antigen is applied to the porous layer, a composition containing said labeled antibody and a solvent not swelling a hydrophilic polymer is applied to the porous layer.

18. The method of claim 13 wherein, after the composition containing said labeled antibody is applied to the porous layer, a composition containing said antigen and a solvent not swelling a hydrophilic polymer is applied to the porous layer.

19. The method of claim 17 or 18 wherein solvent does not dissolve the antigen or antibody present in the porous layer.

20. A method of claim 13, 7, 8, 9, or 10 wherein the protein is albumin.

* * * * *